(12) United States Patent
Hermony

(10) Patent No.: US 10,761,223 B1
(45) Date of Patent: Sep. 1, 2020

(54) SYSTEMS AND METHODS FOR MULTIPLE DETECTOR HEADS IN A SINGLE ARM OR HOUSING

(71) Applicant: GE Precision Healthcare LLC, Wauwatosa, WI (US)

(72) Inventor: Nathan Hermony, Hadera (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/275,077

(22) Filed: Feb. 13, 2019

(51) Int. Cl.
*G01T 1/24* (2006.01)
*G01D 11/24* (2006.01)
*G01T 1/164* (2006.01)
*A61B 6/03* (2006.01)

(52) U.S. Cl.
CPC .............. *G01T 1/244* (2013.01); *A61B 6/037* (2013.01); *G01D 11/245* (2013.01); *G01T 1/1648* (2013.01)

(58) Field of Classification Search
None
See application file for complete search history.

(56) References Cited

U.S. PATENT DOCUMENTS

| | | | |
|---|---|---|---|
| 5,442,179 A | 8/1995 | Ohishi et al. | |
| 5,466,943 A | 11/1995 | Green | |
| 5,757,006 A * | 5/1998 | DeVito | G01T 1/1642 250/363.04 |
| 6,830,387 B2 | 12/2004 | Rife | |
| 6,982,839 B2 | 1/2006 | Schuler et al. | |
| 7,291,841 B2 * | 11/2007 | Nelson | G01T 1/243 250/370.01 |
| 8,338,788 B2 * | 12/2012 | Zilberstein | A61B 6/037 250/363.04 |
| 8,492,725 B2 * | 7/2013 | Zilberstein | G01T 1/1635 250/363.04 |
| 8,748,827 B2 * | 6/2014 | Zilberstein | A61B 6/42 250/363.04 |
| 9,182,507 B2 * | 11/2015 | Hefetz | G06T 11/005 |
| 9,297,913 B2 * | 3/2016 | Grobshtein | G01T 1/1647 |
| 9,322,930 B2 * | 4/2016 | Schellenberg | G01T 1/1644 |
| 9,392,981 B2 * | 7/2016 | Khen | G01T 1/161 |
| 9,402,595 B2 * | 8/2016 | Steinfeld | G01T 1/16 |
| 9,442,197 B2 * | 9/2016 | Shahar | G01T 1/1648 |

(Continued)

OTHER PUBLICATIONS

Spectrum Dynamics Medical, "DS Brochure" D-SPECT Cardiac Imaging System. Mar. 0011-Mar. 2017 (12 pages).

(Continued)

*Primary Examiner* — Thomas R Artman
(74) *Attorney, Agent, or Firm* — The Small Patent Law Group LLC; Dean D. Small

(57) ABSTRACT

A radiation detector assembly is provided that includes a plurality of multi-detector arms (e.g., between 2 and 5), and plural detector head units disposed in each multi-detector arm. Each of the multi-detector arms defines a cavity therein. At least two detector head units are disposed within the cavity of each multi-detector arm. Each detector head unit includes an absorption member and associated processing circuitry, with the processing circuitry configured to generate electronic signals responsive to radiation received by the absorption member. Each detector head unit is configured to pivot along a sweep direction.

20 Claims, 9 Drawing Sheets

(56) References Cited

U.S. PATENT DOCUMENTS

| | | | |
|---|---|---|---|
| 9,482,562 B2 | 11/2016 | Hefetz et al. | |
| 9,689,720 B1 | 6/2017 | Bouhnik et al. | |
| 9,801,597 B2* | 10/2017 | Bouhnik | G06T 7/97 |
| 2004/0251419 A1* | 12/2004 | Nelson | G01T 1/243 |
| | | | 250/370.09 |
| 2011/0026685 A1* | 2/2011 | Zilberstein | G01T 1/1644 |
| | | | 378/197 |
| 2011/0103544 A1* | 5/2011 | Hermony | A61B 6/032 |
| | | | 378/19 |
| 2013/0114792 A1* | 5/2013 | Zilberstein | A61B 6/42 |
| | | | 378/62 |
| 2013/0308749 A1* | 11/2013 | Zilberstein | A61B 6/42 |
| | | | 378/19 |
| 2014/0187923 A1 | 7/2014 | Heukensfeldt Jansen et al. | |
| 2015/0001407 A1* | 1/2015 | Schellenberg | G01T 1/1644 |
| | | | 250/366 |
| 2015/0065873 A1 | 3/2015 | Tsukerman et al. | |
| 2015/0119704 A1* | 4/2015 | Roth | A61B 6/4258 |
| | | | 600/425 |
| 2015/0177392 A1* | 6/2015 | Hefetz | G06T 11/005 |
| | | | 250/362 |
| 2015/0208999 A1* | 7/2015 | Steinfeld | G01T 1/16 |
| | | | 378/205 |
| 2015/0276949 A1* | 10/2015 | Grobshtein | G01T 1/1647 |
| | | | 250/362 |
| 2015/0309184 A1 | 10/2015 | Viscovic et al. | |
| 2015/0342543 A1* | 12/2015 | Khen | G01T 1/161 |
| | | | 250/362 |
| 2016/0077217 A1* | 3/2016 | Shahar | G01T 1/1648 |
| | | | 250/362 |
| 2016/0081641 A1* | 3/2016 | Bouhnik | G06T 7/97 |
| | | | 378/5 |
| 2016/0282152 A1 | 9/2016 | Khen et al. | |
| 2016/0282153 A1 | 9/2016 | Hefetz et al. | |
| 2018/0000431 A1* | 1/2018 | Roth | A61B 6/0407 |
| 2020/0015763 A1* | 1/2020 | Roth | A61B 6/037 |

OTHER PUBLICATIONS

Siegfried, "Nuclear Power Plant Gaseous Waste Treatment System Design", Prepared for the American Society of Mechanical Engineers—Radioactive Waste Systems Committee—Copyright 2012; (55 pages).

Bolmsjo, "Factors affecting the trapping performance of xenon holdup—filters in nuclear medicine applications", Jan-Pubmed Feb. 1982, 9(1):96-105; 1 page.

BIODEX "Pulmonex II Xenon System" 2015 (2 pages).

* cited by examiner

US 10,761,223 B1

SYSTEMS AND METHODS FOR MULTIPLE DETECTOR HEADS IN A SINGLE ARM OR HOUSING

BACKGROUND

The subject matter disclosed herein relates generally to medical imaging systems, and more particularly to the use of multiple detector units within a single arm or housing of a medical imaging system.

In nuclear medicine (NM) imaging, such as single photon emission computed tomography (SPECT) or positron emission tomography (PET) imaging, radiopharmaceuticals may be administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

BRIEF DESCRIPTION

In accordance with an embodiment, a radiation detector assembly is provided that includes a plurality of multi-detector arms (e.g., between 2 and 5), and plural detector head units disposed in each multi-detector arm. Each of the multi-detector arms defines a cavity therein. At least two detector head units are disposed within the cavity of each multi-detector arm. Each detector head unit includes an absorption member and associated processing circuitry, with the processing circuitry configured to generate electronic signals responsive to radiation received by the absorption member. Each detector head unit is configured to pivot along a sweep direction.

In accordance with another embodiment, a radiation detection system is provided that includes a gantry, plural multi-detector arms, and plural detector head units. The gantry defines a bore, and includes a stator and a rotor. The rotor is configured to rotate relative to the stator. The multi-detector arms are radially disposed about the bore and mounted to the rotor. Each multi-detector arm defines a cavity therein, and has a distal portion and a base portion. The base portion is mounted to the rotor, with the distal portion extendable from the base portion. Plural detector head units are disposed within each of the multi-detector arms, with each detector head unit disposed in the cavity in the distal portion of the corresponding multi-detector arm. Each detector head unit includes an absorption member and associated processing circuitry, with the processing circuitry configured to generate electronic signals responsive to radiation received by the absorption member. Each detector head unit is configured to pivot along a sweep direction.

In accordance with another embodiment, a method is provided that includes providing plural multi-detector arms. Each multi-detector arm defines a cavity therein, and has a distal portion and a base portion, with the distal portion extendable from the base portion. The method also includes disposing plural detector head units in the cavity in the distal portion within each of the plural multi-detector arms. Each detector head unit includes an absorption member and associated processing circuitry, with the processing circuitry configured to generate electronic signals responsive to radiation received by the absorption member. Each detector head unit is configured to pivot along a sweep direction. Further, the method also includes mounting the base portion of each of the plural multi-detector arms to a rotor of a gantry about a bore defined by the gantry.

DETAILED DESCRIPTION

Figure 1:
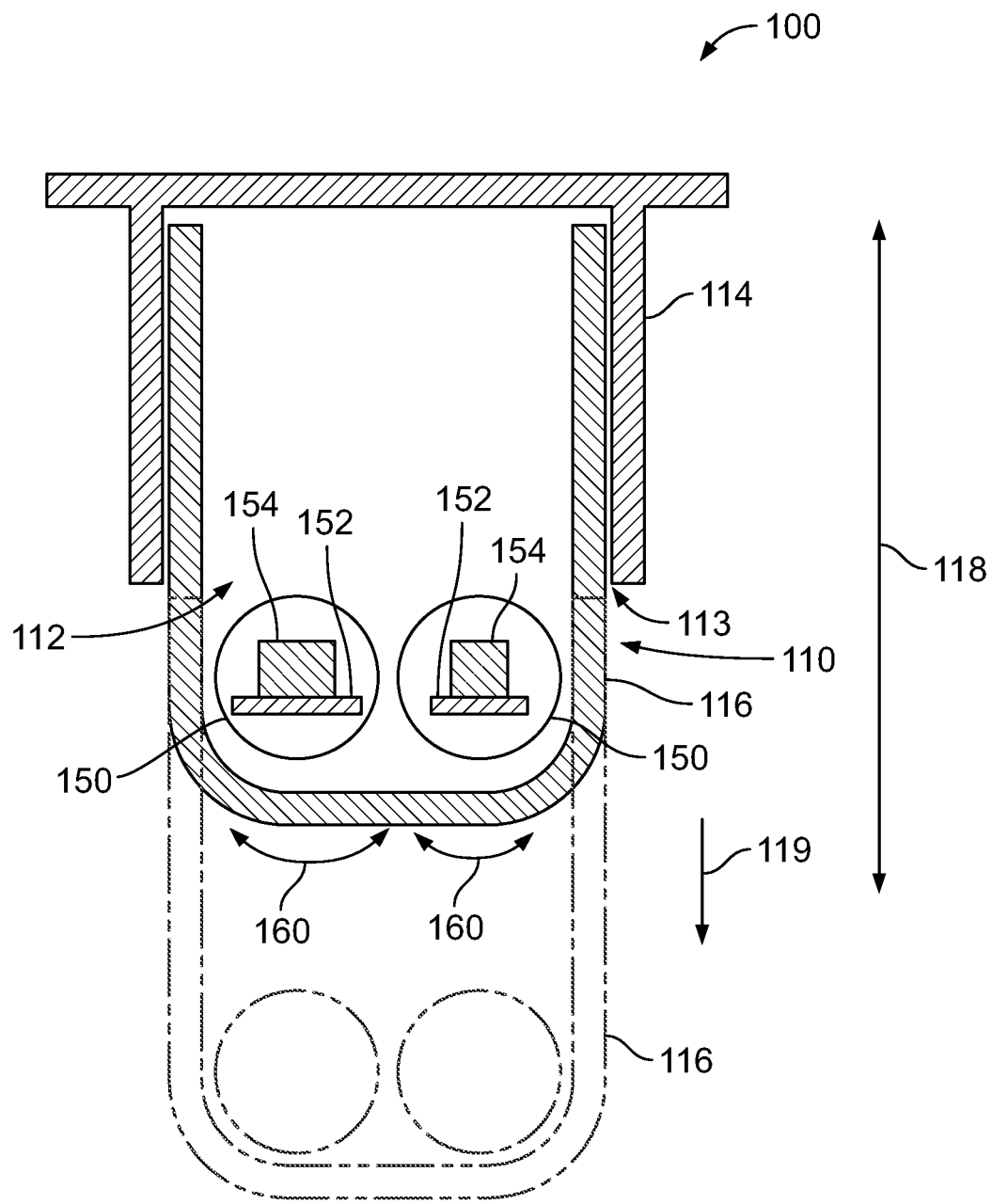
FIG. 1 provides a sectional schematic view of a multi-detector radiation detector assembly according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide detector head assemblies that utilize two or more detector units disposed within a single housing (e.g., articulable arm). For example, a system may have 5 to 8 arms each including two pivoting detector heads, for a total of 10 to 16 pivoting detector heads. Accordingly, the number of moving parts (e.g., articulable arms extending radially inwardly or outwardly) and associated motors and electronics may be reduced while providing a same or increased number of detector units compared to arms with only a single detector, reducing cost and complexity and/or increasing reliability. In some embodiments, a mix of arms with multiple detectors and arms with single detectors may be utilized. Further, in some embodiments arms below a bed may be mounted to a stationary part of the gantry, or mounted to a bed or table. Movement of detector units below the bed may be synchronized with motion (e.g., up-down motion) of the bed in various embodiments.

Generally, use of a greater number of detectors provides more imaging information (and/or a similar amount of imaging information in a shorter amount of time) relative to a lower number of detectors. However, use of a greater number of detectors may increase cost. Articulable arms or other housing can be a substantial portion of the cost and complexity of a system. Accordingly, providing multiple detectors in a single arm or housing reduces total arm cost relative to the number of detectors.

A technical effect of at least one embodiment includes improved image quality (e.g., due to increased numbers of detectors). A technical effect of at least one embodiment includes reduction of imaging time (e.g., due to reduced number of rotational steps required to cover a given volume). A technical effect of at least one embodiment includes reduced cost of manufacture and/or assembly.

FIG. 1 provides a sectional schematic view of a multi-detector radiation detector assembly 100 in accordance with various embodiments. The radiation detector assembly 100 includes a multi-detector arm 110 and plural detector head units 150. Generally, the multi-detector arm 110 supports and positions the plural detector head units 150 relative to an object to be imaged, with the plural detector head units 150 used to acquire radiation imaging information emitted from the object to be imaged. It may be noted that while a single multi-detector arm 110 is depicted in FIG. 1, plural multi-detector arms 110 may be used in various embodiments. For example, as discussed herein, plural multi-detector arms 110 may be mounted along a circumference of a bore defined by a gantry. It may further be noted that while the multi-detector arm 110 depicted in FIG. 1 has two detector head units 150 disposed therein, more than two detector head units 150 may be disposed within a multi-detector arm 110 in various embodiments. For example, in some embodiments, five or more detector head units 150 may be disposed within the multi-detector arm 110.

The multi-detector arm 110 defines a cavity 112. The cavity 112 in the illustrated example is defined within an open space bounded by an arm housing 113. In the illustrated example, the multi-detector arm 110 includes a base portion 114 and a distal portion 116. The depicted detector head units 150 are disposed in the distal portion 116, which is extendable from the base 114 along a length 118 the multi-detector arm, such that the length 118 is variable. For example, the detector head unit 150 in FIG. 1 is shown in solid lines in a retracted position, but may be advanced to an extended position (and/or intermediate positions between the retracted and extended positions) shown in phantom lines along direction 119 (e.g., toward a center of a bore of a gantry to which the multi-detector arm 110 is mounted).

The plural detector head units 150 of the radiation detector assembly 100 are disposed within the cavity 112 of the multi-detector arm 110. In the illustrated embodiment, the detector head units 150 are disposed adjacent to each other, in the distal portion 116, at a similar position along the length 118 of the multi-detector arm 110. Each detector head unit 150 includes an absorption member 152 and associated processing circuitry 154. The absorption member 152 is configured to receive radiation from an object being imaged, and is communicatively coupled to the processing circuitry 154. Generally, the processing circuitry 154 generates electronic signals responsive to radiation received by the absorption member 152. The absorption member 152 is configured to receive radiation (e.g., radiation passing from an object to be imaged through a collimator (not shown)) and to generate electronic signals, in conjunction with the processing circuitry 154, in response to radiation received and/or absorbed by the absorption member 152. The absorption member 152 may be formed of a semiconductor material, such as Cadmium Zinc Telluride (CdZnTe), often referred to as CZT, Cadmium Telluride (CdTe), or Silicon (Si), among others. The electronic signals may be used, for example, to determine counts corresponding to uptake of a radiopharmaceutical for different locations within an object being imaged, and used to reconstruct an image of the object.

Each detector head unit 150 is configured to pivot along a sweep direction 160. For example, each detector head unit 150 may be mounted to a corresponding rotor of a detector head assembly disposed within the multi-detector arm 110. (For additional discussion regarding aspects of an example detector head unit and rotor of a detector head assembly, see FIGS. 9 and 10, and related discussion, as well as U.S. Pat. No. 9,689,720, entitled "Reduced Airborne Contamination Detector Heads," the entire disclosure of which is hereby incorporated by reference in its entirety.) Accordingly, the view angle of the absorption member 152 relative to an object being imaged may be changed as the detector head unit 150 is pivoted along the sweep direction 160, and radiation emitted from the object may be absorbed and detected from different directions or different fields of view by a given detector head unit 150 as it sweeps. As used herein, rotating about a sweep axis, or sweeping, may be understood as the rotation of a detector head unit (or portion thereof) about an axis passing through a central portion of the detector head unit along the length of the detector head unit. An example of such an axis is provided by axis 906 discussed in connection with FIGS. 9 and 10 below. In various embodiments, each detector head unit 150 is configured to pivot or sweep independently of other detector head units disposed with the same multi-detector arm. For example, each detector head unit 150 may include or have associated therewith a motor configured to pivot the detector head unit 150 along the sweep direction 160.

Figure 2:
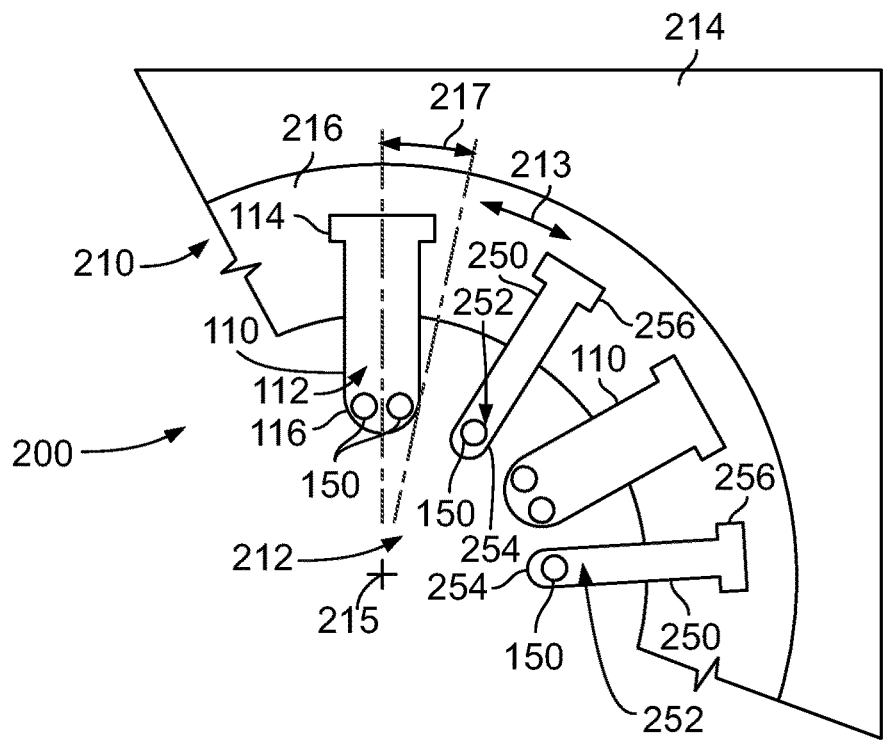
FIG. 2 provides a schematic partial view of a radiation detection system that includes a plurality of multi-detector arms according to an embodiment.

In various embodiments, the multi-detector arm 110 is used in connection with multiple additional detector arms, some or all of which may be configured generally similarly to the multi-detector arm 110. FIG. 2 depicts a schematic partial view of a radiation detection system 110 that includes a plurality of multi-detector arms 110 in accordance with various embodiments. As seen in FIG. 2, the depicted example embodiment includes a gantry 210, plural multi-detector arms 110, and plural detector head units 150.

The gantry 210 defines a bore 212. The bore 212 is sized to accept an object (e.g., human patient) to be imaged. The gantry 210 includes a stator 214 and a rotor 216. The rotor 216 is configured to rotate relative to the stator 214. For example, the stator 214 may be mounted or fixed to a floor or other structure, and the rotor 216 may rotate about a center of the bore 212 to position the multi-detector arms 110. In various embodiments, the rotor 216 is rotated in two or more steps, with imaging information collected while the rotor 216 is stopped at each of the steps. For example, the rotor 216 may move a rotational step angle 217 between a first and second rotational step. Generally, the gantry 210 is used to position and support the multi-detector arms 110 about the bore 212 to image an object (e.g., human patient disposed within the bore).

The depicted radiation detection system 200 includes plural multi-detector arms 110. (See also FIG. 1 and related discussion.) The multi-detector arms 110 of the illustrated example are radially disposed about the bore 212 of the gantry 210, and are mounted to the rotor 216 of the gantry 210. Each depicted multi-detector arm 110 defines a cavity 112. The multi-detector arms 110 extend along corresponding axes from a mounting location on the rotor 216 toward a center of the bore 212. Each depicted multi-detector arm 110 of the radiation detection system 200 has a distal portion 116 and a base portion 114, with the base portion 114 mounted to the rotor 216. The distal portion 116 is extendable from the base portion 114 toward (or away) from the center of the bore 212. Accordingly, the distal portion 116 may be actuated relative to the base portion 114 (which is mounted to the rotor 216) radially inwardly and outwardly relative to the center or interior of the bore 212 to position detector head units 150 within the distal portion 116 at a desired distance from an object disposed in the bore 212 for imaging.

The depicted radiation detection system 200 includes detector head units 150. (See also FIG. 1 and related discussion.). Plural detector head units 150 (two in the illustrated example) are disposed within each of the multi-detector arms 110, with each detector head unit 150 disposed within the cavity 112 in the distal portion 116 of the corresponding multi-detector arm. Each detector head unit 150 includes an absorption member 152 and associated processing circuitry 154, with the processing circuitry 154 configured to generate electronic signals responsive to radiation received by the absorption member 152. (See FIG. 1.) Each detector head unit 150 is configured to pivot along a sweep direction 160. (See FIG. 1.) As the detector head units 150 are mounted via the multi-detector arms 110 to the rotor 216, the detector head units 150 may be pivoted within their corresponding multi-detector arm 110 about their own axis as part of a sweeping movement, and also may be pivoted about a center 215 of the bore 212 with their corresponding multi-detector arm 110. To position a given detector head unit 150 for imaging, the rotor 216 may be pivoted to a desired position (or step), and the distal portion 116 of the multi-detector arm 110 actuated radially inwardly or outwardly with respect to the bore 212 to position the detector head unit 150 a desired distance from an object being imaged. Then, with detector head unit 150 at a desired location, the detector head unit 150 may be swept over an acquisition range to acquire imaging information emitted from the object being imaged.

Use of plural multi-detector arms 110 allows for reducing the number of arms required per detector unit, reducing overall cost relative to the number of views of imaging information capable of being acquired. However, use of single detector arms can provide additional flexibility in the individual positioning of detector units with respect to each other, and that the cost of an individual detector arm having only a single detector will generally be lower than the cost of an otherwise similar individual multi-detector arm having multiple detectors. Accordingly, it may be noted that, in some examples, single detector arms may be used in conjunction with multi-detector arms.

In the example depicted in FIG. 2, the radiation detection system 200 includes single detector arms 250 radially disposed about the bore 212 and mounted to the rotor 216. Each single detector arm 250 includes on a single detector head unit 150 disposed therein. The single detector arms 250 in the illustrated embodiment are generally similar to the multi-detector arms 110 (e.g., are mounted to the rotor 216, are of similar length, are extendable from a base 256 radially inwardly/outwardly with respect to a center of the bore 212), but have only a single detector head unit 150 disposed in a corresponding cavity 252 of a distal end 254 of a given single detector arm 250. In the illustrated embodiment, the single detector arms 250 alternate with multi-detector arms 110 along a circumference 213 of the rotor 216.

Various embodiments include multi-arm detector arms 110 mounted to a gantry in a predetermined spatial relationship with each other (and, optionally, single detector arms 250 may also be mounted to the gantry in a predetermined spatial relationship with the multi-detector arms 110). For example, detector arms may be evenly distributed about the bore of a gantry. The particular number of each type of detector arm and location of each detector arm may be selected as appropriate to suit particular applications (e.g., based on cost, size or range of sizes of object(s) to be imaged, desired image quality, desired number of rotational steps of gantry, or the like).

Figure 3:
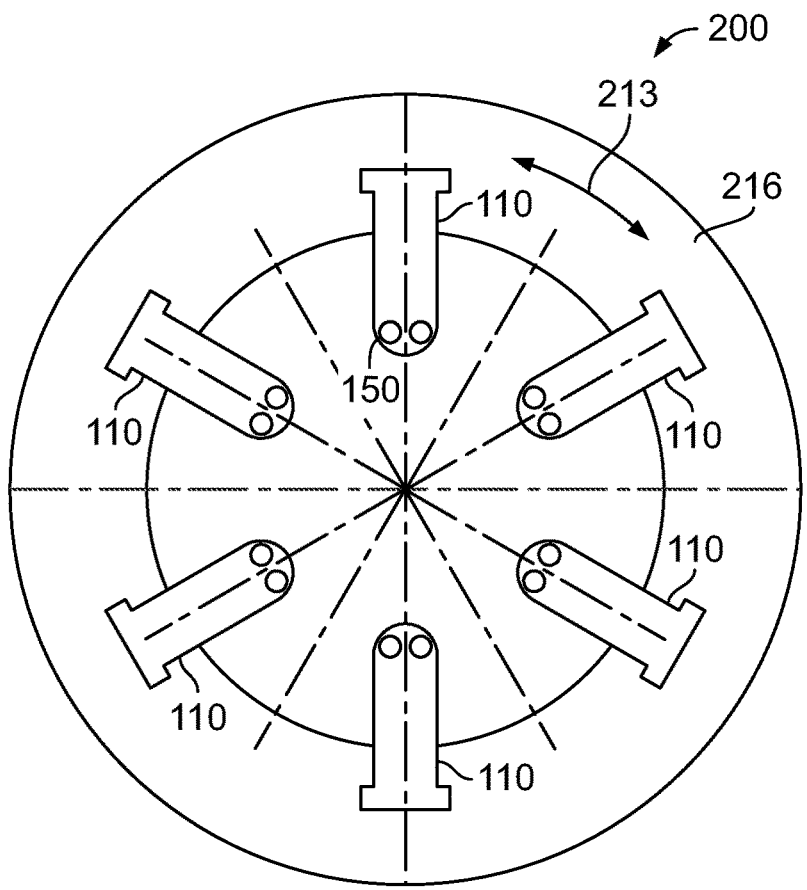
FIG. 3 provides a schematic view of a radiation detection system includes 6 multi-detector arms evenly distributed about the circumference of a rotor according to an embodiment.

FIG. 3 depicts an example embodiment in which the radiation detection system 200 includes 6 multi-detector arms 110 evenly distributed about the circumference 213 of the rotor. In the illustrated example, each multi-detector arm 110 includes 2 detector head units 150. Accordingly, the example of FIG. 3 includes a total of 12 detector head units 150. Such an example system includes fewer arms compared to a 12 single detector arm system while providing a similar number of total detector heads.

Figure 4:
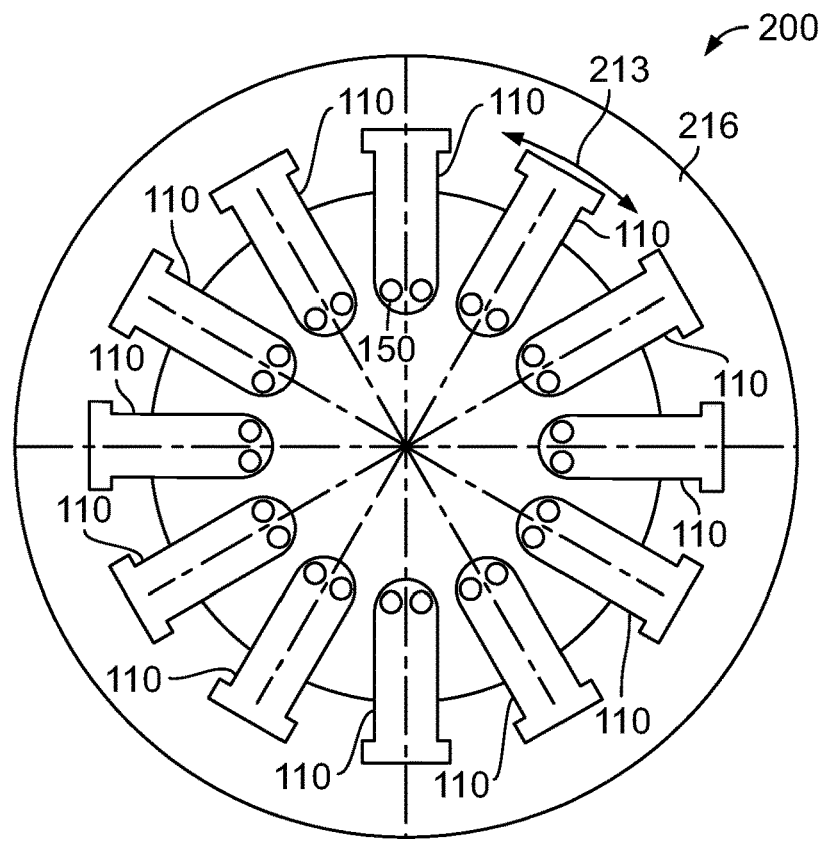
FIG. 4 provides a schematic view of a radiation detection system includes 12 multi-detector arms evenly distributed about the circumference of a rotor according to an embodiment.

FIG. 4 depicts an example embodiment in which the radiation detection system 200 includes 12 multi-detector arms 110 evenly distributed about the circumference 213 of the rotor. In the illustrated example, each multi-detector arm 110 includes 2 detector head units 150. Accordingly, the example of FIG. 4 includes a total of 24 detector head units 150. Such an example system includes the same number of arms as a 12 single detector system but provides twice as many detector heads.

Figure 5:
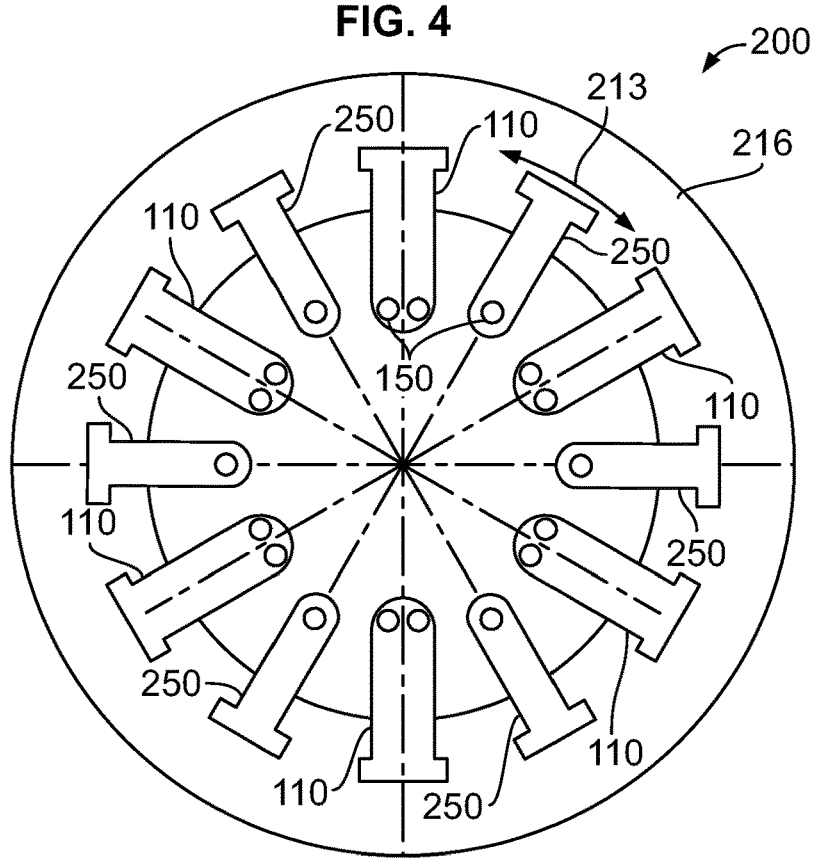
FIG. 5 provides a schematic view of a radiation detection system includes 6 multi-detector arms and 6 single detector arms distributed about the circumference of a rotor according to an embodiment.

FIG. 5 depicts an example embodiment in which the radiation detection system 200 includes 6 multi-detector arms 110 and 6 single detector arms 250 alternating with each other and evenly distributed about the circumference 213 of the rotor. Accordingly, the example of FIG. 5 includes a total of 18 detector head units 150. Such an example system uses alternating multi-detector arms 110 and single detector arms 250 along the circumference 213 of the rotor 216. Use of single detector arms 250 in connection with multi-detector arms 110 provides additional flexibility in terms of imaging capability. For example, the single detector arms 250 may be retracted or removed to provide similar imaging capability to the example of FIG. 3, or the single detector arms 250 may be utilized to provide additional detectors.

As mentioned above, the particular configuration of a given system (e.g., number of each type of detector arm, location of each detector arm) may be selected as appropriate to suit particular applications. The chart below provides a comparison of different numbers of rotational steps of a rotor of a gantry required for full coverage by a detector system, including the examples discussed in connection with FIGS. 3-5 in comparison with a system having 12 evenly spaced single-detector arms. Generally, the more arms and/or detector units utilized, the lower number of rotational steps will be required. The example values below are for system utilizing detector heads having 78 millimeter diameters, with adjacent detector head units in the same multi-arm detector having 80 millimeter distances between their centers.

|  | 12 single-detector arms | 6 two-detector arms (example of FIG. 3) | 6 two-detector arms and 6 single-detector arms (example of FIG. 5) | 12 two-detector arms (example of FIG. 4) |
| --- | --- | --- | --- | --- |
| Detectors spaced around 800 millimeter diameter circle | 4 rotational steps required (with small overlap) | 3 rotational steps required (with overlap) | 2 rotational steps required (with small gap) | 1 rotational step required (with overlap) |
| Detectors spaced around 700 millimeter diameter circle | 4 rotational steps required (with overlap) | 2 rotational steps required (no gap) | 2 rotational steps required (no gap) | 1 rotational step required (with overlap) |

As seen above, arrangements with more arms and/or detectors provide more acquisition capability and/or fewer rotational steps for more coverage and/or lower acquisition time, as well as more flexibility, while using fewer arms lowers cost and complexity. It may be noted that the above examples are provided for illustrative purposes by way of example. The particular arrangement for a given application can be selected based on the requirements of the given application.

Figure 6:
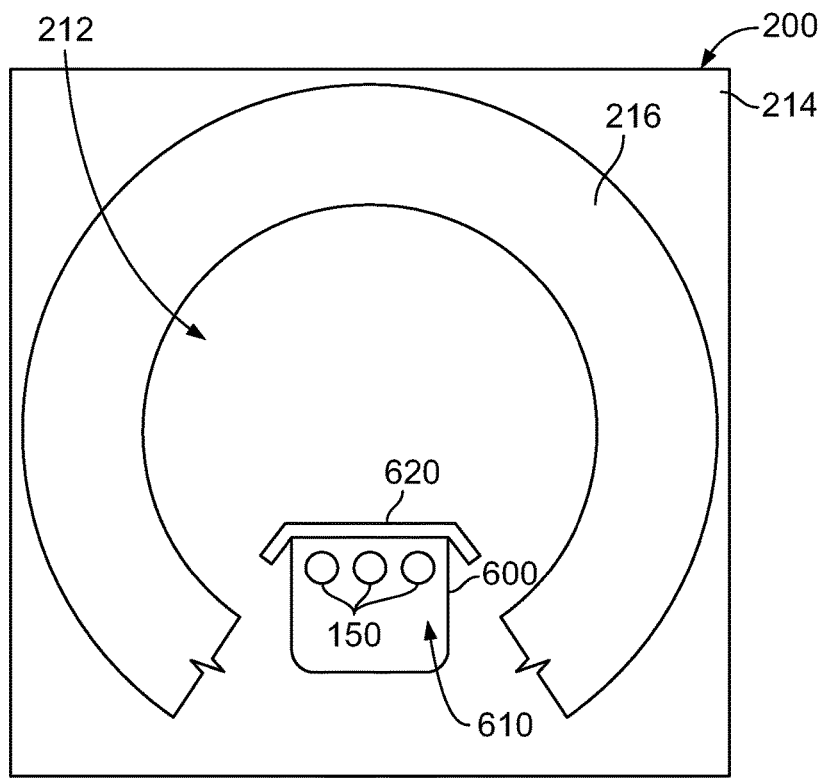
FIG. 6 provides a schematic view of a radiation detection system that includes a non-rotating multi-detector housing according to an embodiment.
Figure 7:
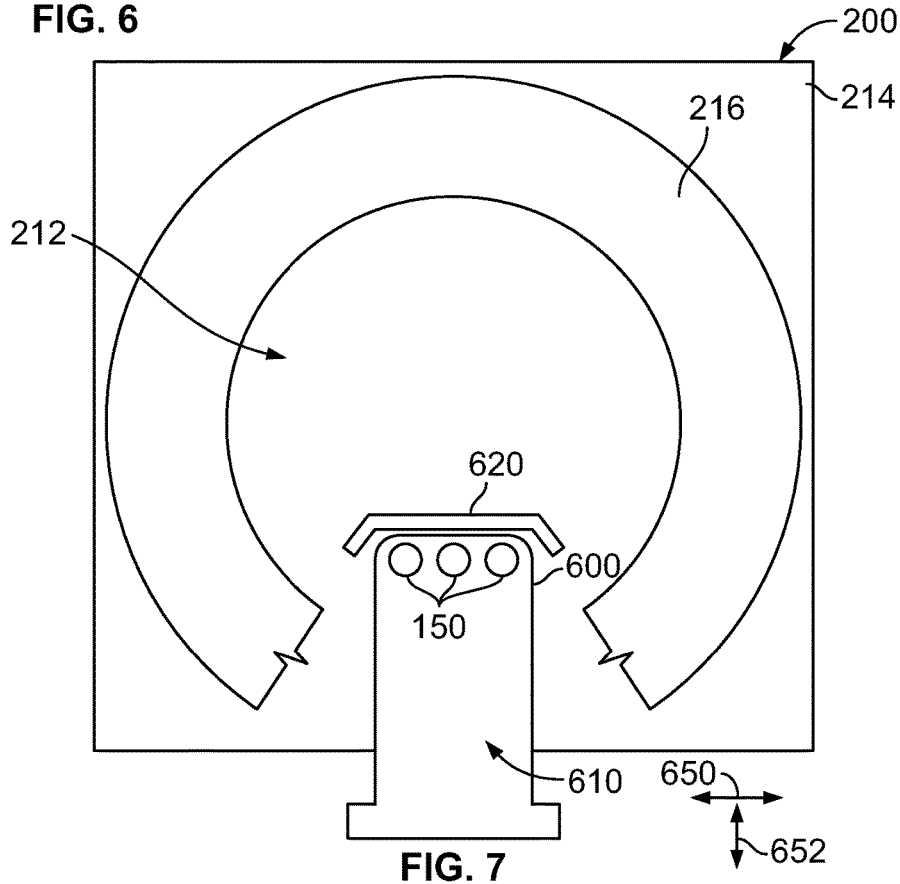
FIG. 7 provides a schematic view of a radiation detection system that includes a non-rotating multi-detector housing according to an embodiment.

In addition to the above discussed examples of detector arms that are mounted to a rotor and accordingly rotate about the center of a bore with a rotor, additional detectors are provided that may not be fixed to or rotate with the rotor in some embodiments. For example, detectors located under a bed or table may be difficult or inconvenient to place close to an object being imaged while rotating. FIGS. 6 and 7 provided examples of radiation detection systems that include non-rotating arms disposed under a bed.

FIG. 6 provides a schematic view of an example of the radiation detection system 200 that includes a non-rotating multi-detector housing 600 that does not rotate with a rotor, in accordance with various embodiments. The non-rotating multi-detector housing 600 includes a cavity 610 in which three detector units 150 are disposed. Other numbers of detector units 150 may be utilized in various embodiments. Generally, the non-rotating multi-detector housing 600 may be understood as having at least two detector units 150 disposed therein. The non-rotating multi-detector housing 600 does not rotate with the rotor 216, but is instead rotationally fixed with respect to the stator 214. It may be noted that, in various embodiments, the non-rotating multi-detector housing 600 is configured to be adjustable along at least one linear or lateral direction. For example, in the illustrated example, the non-rotating multi-detector housing 600 is adjustable along a horizontal direction 650 (e.g., generally parallel to a table 620 under which multi-detector housing 600 is located) and a vertical direction 652 (e.g., generally perpendicular to the table 620). In various embodiments, the multi-detector housing may move laterally or linearly with the table 620, or independently of the table 620.

In the example, of FIG. 6, the non-rotating multi-detector housing 600 is mounted to the table 620. It may be noted that in various embodiments, the table 620 may be configured to move in and out of the bore 212 of the gantry 210 (e.g., for placement or removal of an object to be imaged on the table 620.)

FIG. 7 provides a schematic view of another example of the radiation detection system 200 that includes a non-rotating multi-detector housing 600 that does not rotate with a rotor, in accordance with various embodiments. In the example depicted in FIG. 7, the non-rotating multi-detector housing 600 is mounted to the stator 214. For the example depicted in FIG. 7, the non-rotating multi-detector housing 600 may be moved independently of the table 620 (e.g., along horizontal direction 650 and/or vertical direction 652.

Figure 8:
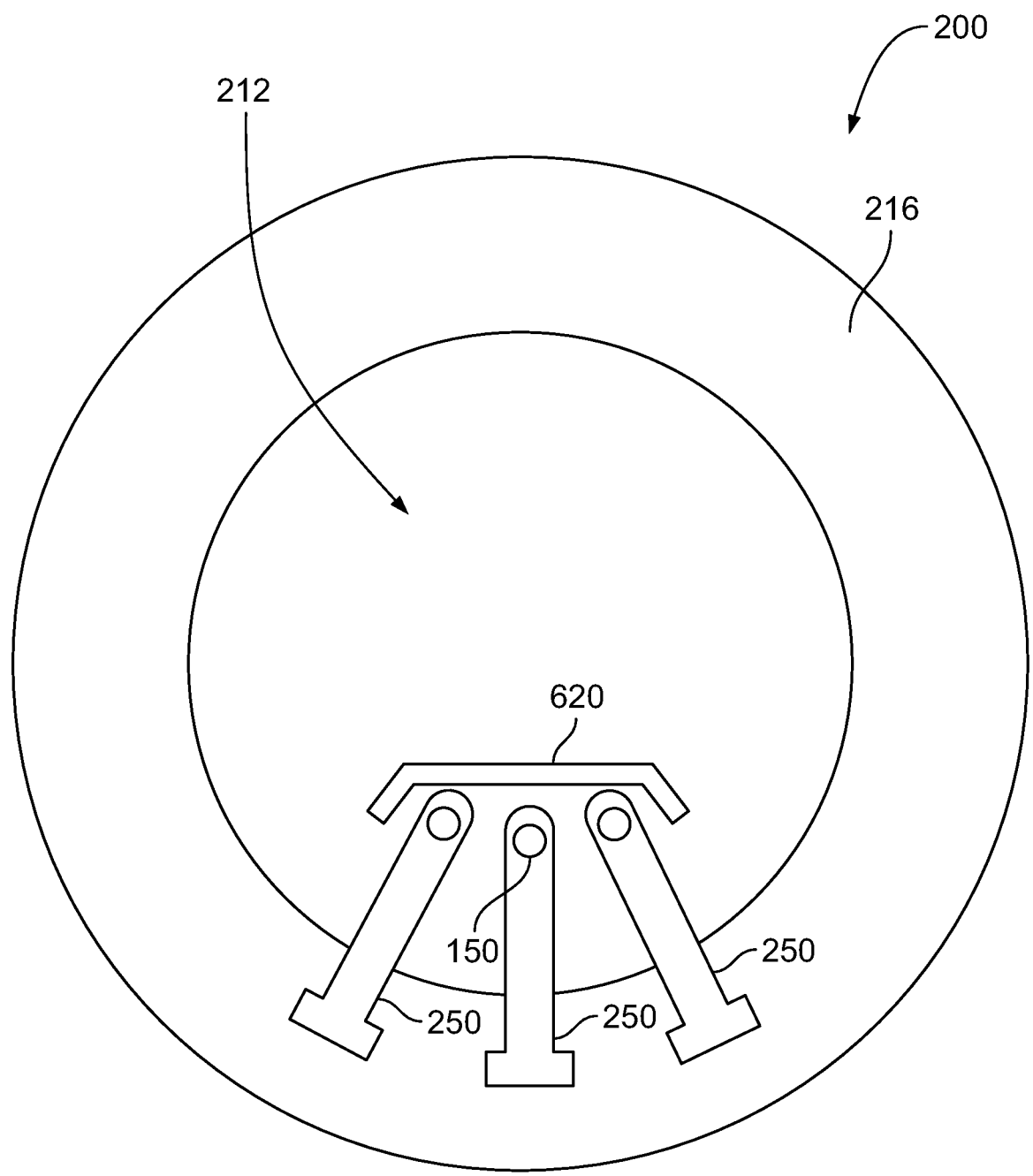
FIG. 8 provides a schematic view of a radiation detection system that includes single detector arms disposed underneath a table according to an embodiment.

It may be noted that, in various embodiments, rotating detector arms may be utilized beneath a table or bed. FIG. 8 provides a schematic view of the radiation detection system 200 that includes single detector arms 250 disposed underneath a table 620, in accordance with various embodiments. As seen in FIG. 8, the depicted example detection system 200 includes three single detector arms 250 disposed underneath the table 620, and coupled to the rotor 216 so that the three single detector arms 250 disposed underneath the table 620 rotate with the rotor 216. To accommodate different detector positions relative to the underside of the table 620, the single detector arms 250 may be maintained at a single sufficient to clear the underside of the table 620 regardless of rotational step position of the gantry 210, or the length of each single detector arm 250 disposed underneath the table 620 may be adjusted based on rotational step position to avoid contact with the table 620.

Figure 9:
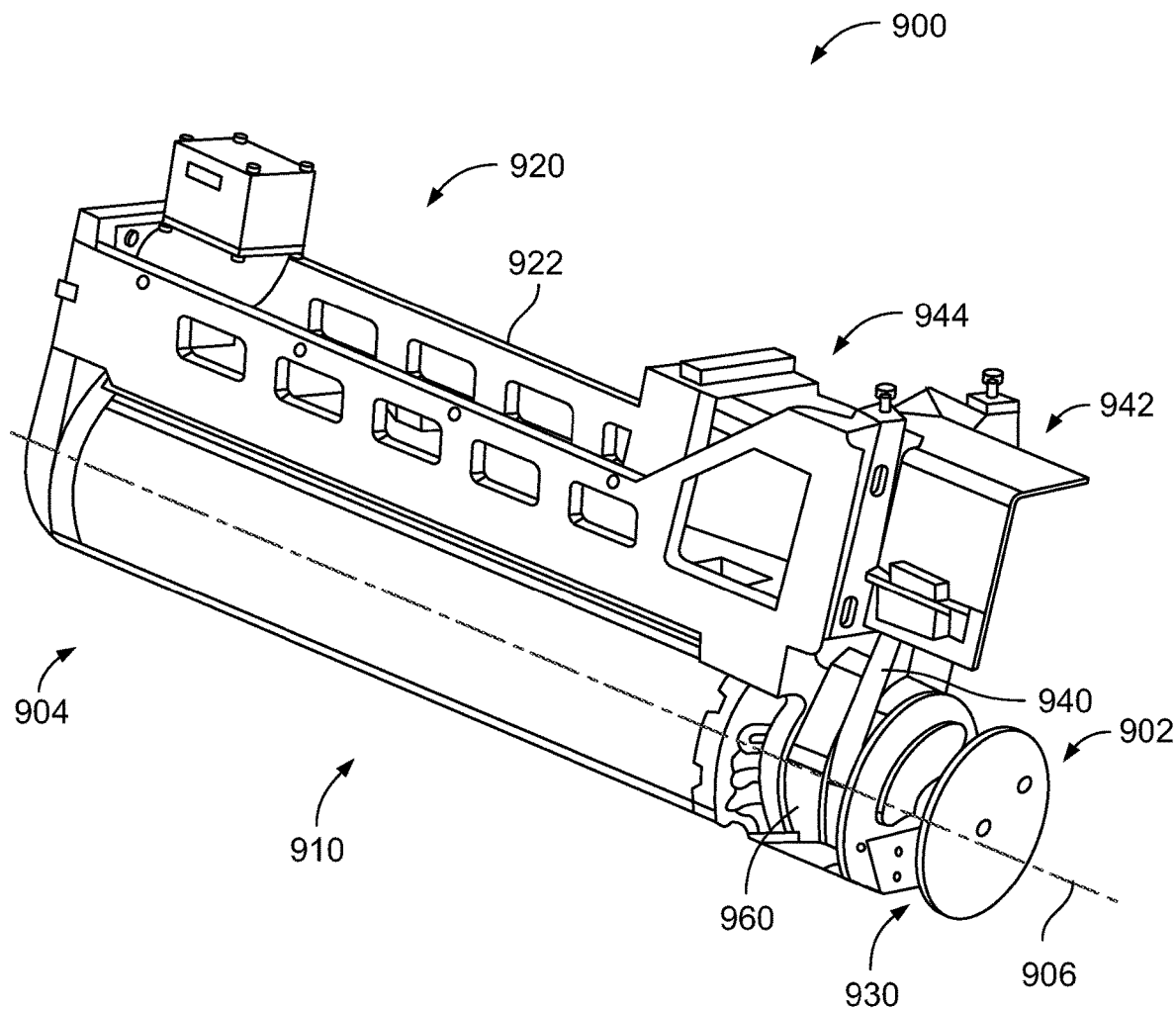
FIG. 9 provides a perspective schematic view of a radiation detector head assembly according to an embodiment.
Figure 10:
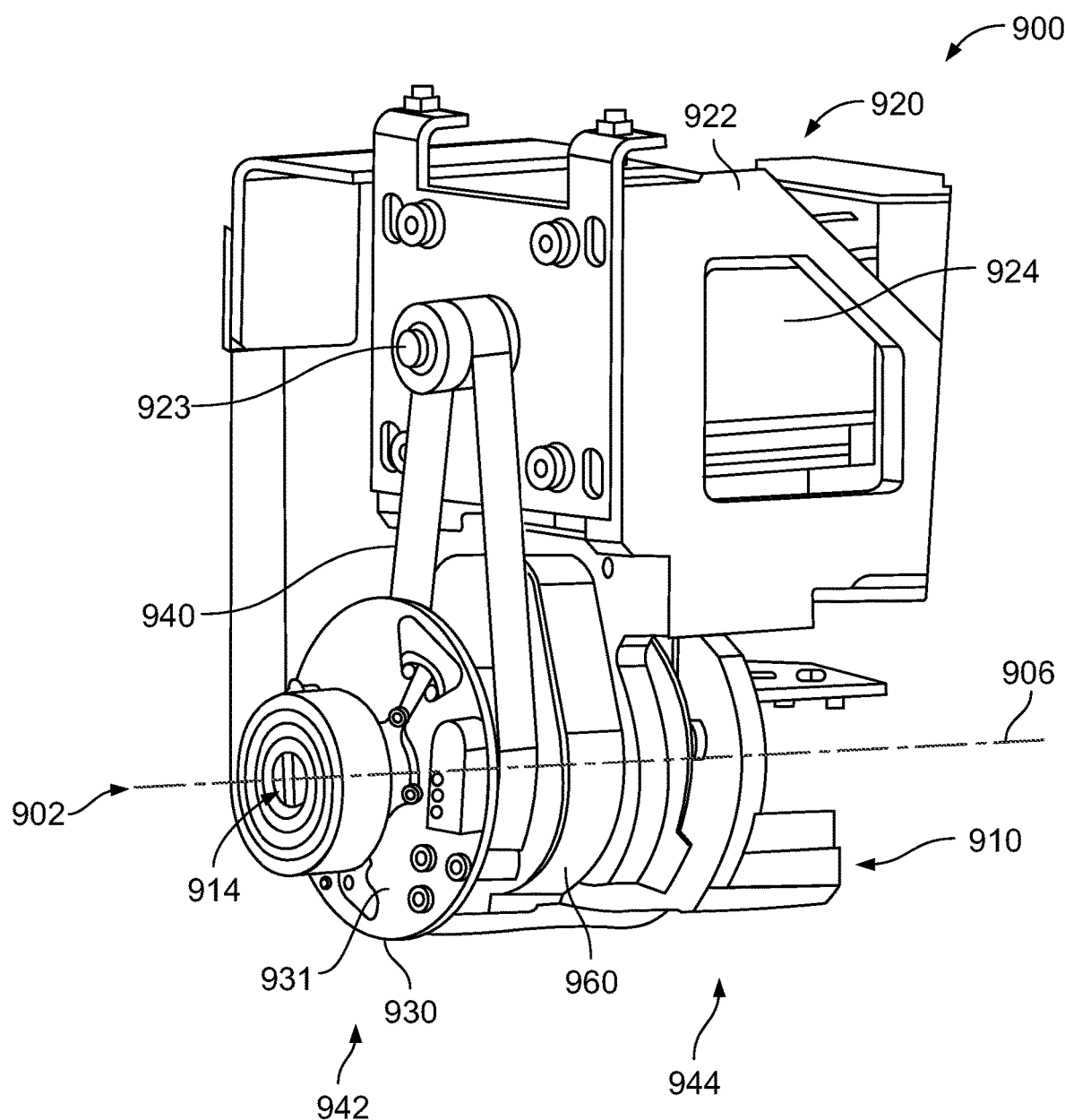
FIG. 10 provides an enlarged view of a first end of the radiation detector head assembly of FIG. 9.

FIGS. 9 and 10 provide additional detail of an example radiation detector head assembly 900. It may be noted that aspects of the radiation detector head assembly 900 may be implemented in connection with multi-detector arm 110 and/or single detector arm 250, and that the radiation detector head assembly 900 may be disposed within the cavity 112 of the multi-detector arm 110 (along with one or more additional radiation detector head assemblies 900). It may also be noted that aspects of the radiation detector head assembly 900 mounted to and/or forming a part of the rotor assembly 910 of the radiation detector head assembly 900 may be included in examples of the detector head unit 150.

FIG. 9 provides a perspective schematic view of a radiation detector head assembly 900 in accordance with various embodiments, and FIG. 10 provides an enlarged view of a first end of the radiation detector head assembly 900. As seen in FIGS. 9 and 10, the radiation detector head assembly 900 defines a first end 902 and a second end 904, with the second end 904 disposed opposite the first end 902 along an axis 906. The radiation detector head assembly 900 includes a rotor assembly 910, a stator assembly 920, rotor processing circuitry 930, and a drive belt 940. The rotor assembly 910 is configured to pivot about the axis 906, and includes one or more detectors. The stator assembly 920 does not rotate. In the depicted embodiment, the rotor processing circuitry 930 rotates with the rotor assembly 910. The drive belt 940 is coupled to the rotor assembly 910 and is used to rotate the rotor assembly 910.

The rotor assembly 910 includes at least one detector unit 912 extending along the axis 906 of the radiation detector head assembly 900. The detector unit 912 may be configured generally similarly to aspects of the detector head unit 150 discussed herein. The rotor assembly 910 is configured to pivot about a shaft 914. It may be noted that the shaft 914 need not run along the entire length of the rotor assembly 910. For example, the shaft 914 may include discontinuous shaft portions.

The depicted stator assembly 920 includes a frame 922 and a motor 924. The motor 924 is mounted to the frame 922. The motor 924 is coupled to the rotor assembly 910 (e.g., via drive belt 940). The motor 924 is configured to pivot the rotor assembly 910 about the axis 906. For example, in the illustrated embodiment motor shaft 923 of the motor 924 may provide an input to the drive belt 940, which turns the shaft 914 (e.g., first shaft portion 915) of the rotor assembly 910 to sweep the at least one detector unit 912 over an object to be imaged during acquisition of imaging information.

The rotor processing circuitry 930 is operably coupled to the rotor assembly 910, and configured to rotate with the rotor assembly 910. For example, in the illustrated embodiment, the rotor processing circuitry 930 is mounted to the shaft 914 and pivots about the axis 906 along with the rotor assembly 910. Generally, the rotor processing circuitry 930 is configured to exchange information between the rotor assembly 910 and one or more processors that do not rotate with the rotor assembly 910 (e.g., to provide control information from the one or more processors to the rotor assembly 910, to provide acquired imaging information from one or more detectors (e.g., detector unit 912) of the rotor assembly 910 to the one or more processors). For example, the rotor processing circuitry 930 may be used to receive imaging information from the processing circuitry of individual detector units, and to provide the imaging information from the individual detector units to one or more centralized processors for generating an image. In the illustrated embodiment, the rotor processing circuitry 930 includes a board 931 (e.g., a printed circuit board) that is in electrical communication with one or more additional boards on a gantry (not shown in FIGS. 9-10) to which the detector head assembly 900 is mounted.

The drive belt 940 couples the motor 924 with the rotor assembly 910. In the illustrated embodiment, the drive belt 940 is coupled to the motor shaft 923 and the shaft 914 of the rotor assembly 910, with the motor shaft 923 used to drive the shaft 914 via the drive belt 940 to pivot or sweep the rotor assembly 910 a desired amount. As seen in FIGS. 9 and 10, the drive belt 940 is interposed between the first end 902 and the second end 904 of the radiation detector head assembly 900. The drive belt 940 defines an outboard side 942 that interposed between the drive belt 940 and the first end 902. The drive belt 940 also defined an inboard side 944 that is interposed between the drive belt 940 and the second end 904. The depicted rotor processing circuitry 930 is disposed on the outboard side 942. Positioning the rotor processing circuitry 930 on the outboard side 942 in various embodiments provides for easier access and maintenance of the processing circuitry. It may be noted that additional electronic components may be used, and positioned either outboard or inboard of the drive belt 940 in various embodiments. For example, in the illustrated example, an encoder 960 is disposed immediately inboard of the drive belt 940.

Also in the illustrated example, the motor 924 is disposed on the inboard side 944, or inboard of the drive belt 940. Positioning the motor 924 inboard of the drive belt 940 as seen in the illustrated embodiment provides for convenient mounting within the frame 922, and also allows for relatively shorter shaft lengths, reducing deflection of one or more shafts and/or reducing the cost of the shafts. Further, positioning the motor 924 inboard also reduces the overall length of the radiation detector head assembly 900, allowing for more efficient coverage of an object being imaged over a length extending along the axis 906.

Figure 11:
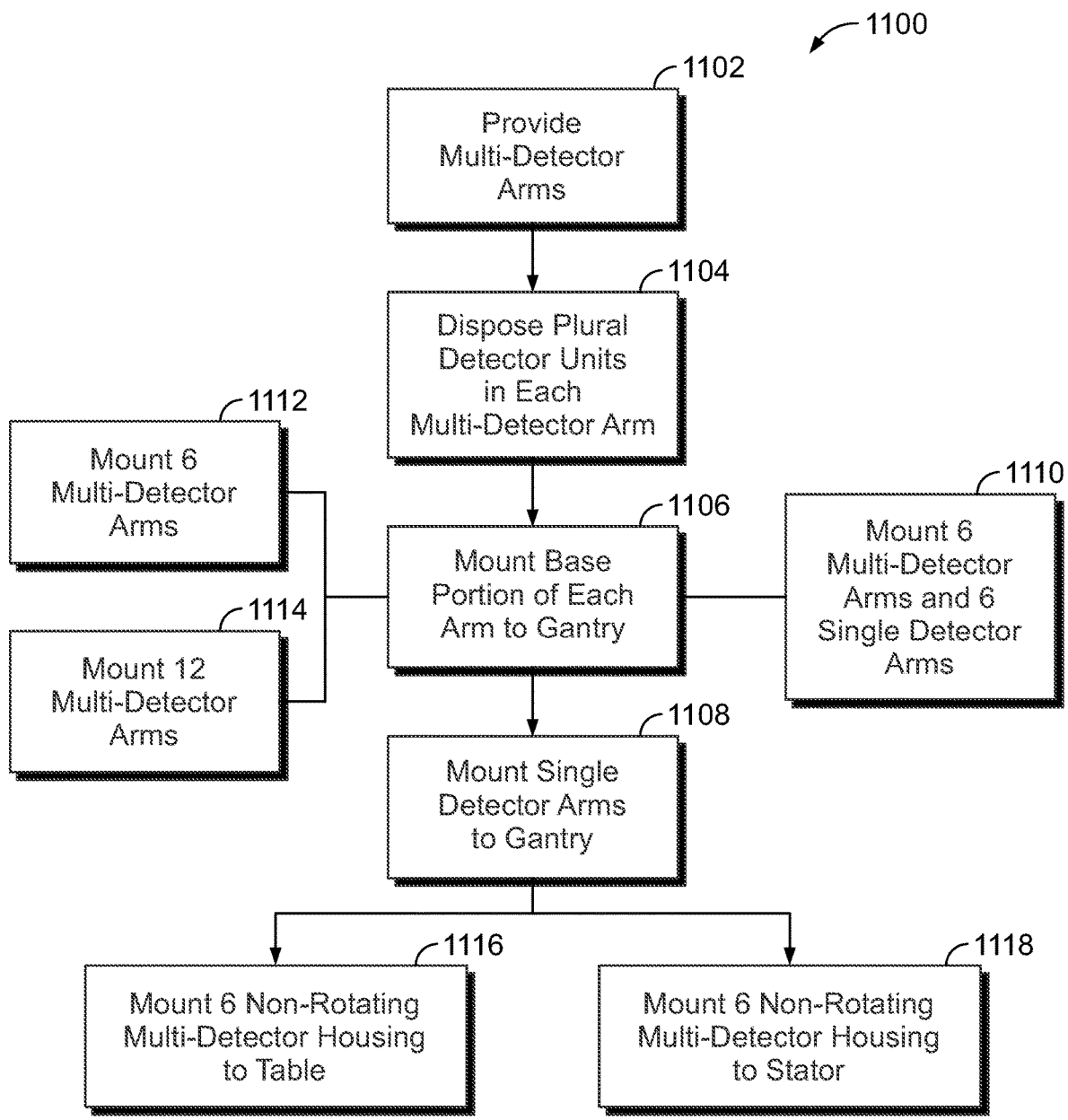
FIG. 11 provides a flowchart of a method according to an embodiment.

FIG. 11 provides a flowchart of a method 1100 for forming, assembling, and/or otherwise providing a radiation detector head assembly, in accordance with various embodiments. The method 1100, for example, may employ or be performed by or with structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 1102, plural multi-detector arms (e.g., multi-detector arms 110) are provided. Each multi-detector arm defines a cavity. Also, each multi-detector arm has a distal portion and a base portion, with the distal portion extendable from the base portion.

At 1104, plural detector head units (e.g., detector head units 150) are disposed within each of the multi-detector arms. The detector head units are disposed within the cavity in the distal portion of the corresponding multi-detector arm. As discussed herein, each detector head unit includes an absorption member and associated processing circuitry, with the processing circuitry configured to generate electronic signal responsive to radiation received by the absorption member. Each detector head unit is configured to pivot along a sweep direction.

At 1106, the base portion of each of the multi-detector arms is mounted to a rotor of a gantry (e.g., gantry 210). The gantry defines a bore (e.g., for positioning of an object to be imaged), and the multi-detector arms are mounted to the rotor about the bore of the gantry. The multi-detector arms in various embodiments are oriented with the distal portion extending from the base and directed toward a center of the bore. Accordingly, varying the amount of extension of the distal portion from the base portion for a given detector unit adjusts the position of the detector unit radially inwardly and outwardly (e.g., to a position close to an object being imaged). Various numbers of multi-detector arms (and, optionally, additional single detector arms) may be mounted to the rotor in various embodiments.

For example, at 1108 of the illustrated embodiment, single detector arms are mounted to the rotor radially about the bore. Each single detector arm has only a single detector head unit disposed therein. In some embodiments, at least some of the single detector arms alternate with multi-detector arms along a circumference of the rotor. For example, at 1110, 6 multi-detector arms and 6 single detector arms are mounted to the rotor, with the arms arranged in an alternating layout along the circumference of the rotor (e.g., a multi-detector arm at a 12:00 position, a single detector arm at a 1:00 position, a multi-detector arm at a 2:00 position, a single detector arm at a 3:00 position, and so on).

As another example, at 1112, 6 multi-detector arms are mounted evenly distributed about the circumference of the rotor (e.g., a multi-detector arm at a 12:00 position, a multi-detector arm at a 2:00 position, a multi-detector arm at a 4:00 position, and so on). As one more example, at 1114, 12 multi-detector arms are mounted evenly distributed about the circumference of the rotor (e.g., a multi-detector arm at a 12:00 position, a multi-detector arm at a 1:00 position, a multi-detector arm at a 2:00 position, and so on).

It may be noted that additional detector units may be utilized in various embodiments. For example, in the illustrated embodiment, at 1116, a non-rotating multi-detector housing (e.g., non-rotating multi-detector housing 600) is mounted to a table disposed within the bore of the gantry. The non-rotating multi-detector housing includes at least two detector heads. It may be noted that the non-rotating multi-detector housing need not be mounted to the table, but may be otherwise mounted in other embodiments. For example, at 1118, alternatively, the non-rotating multi-detector unit is mounted to a stator of the gantry.

Figure 12:
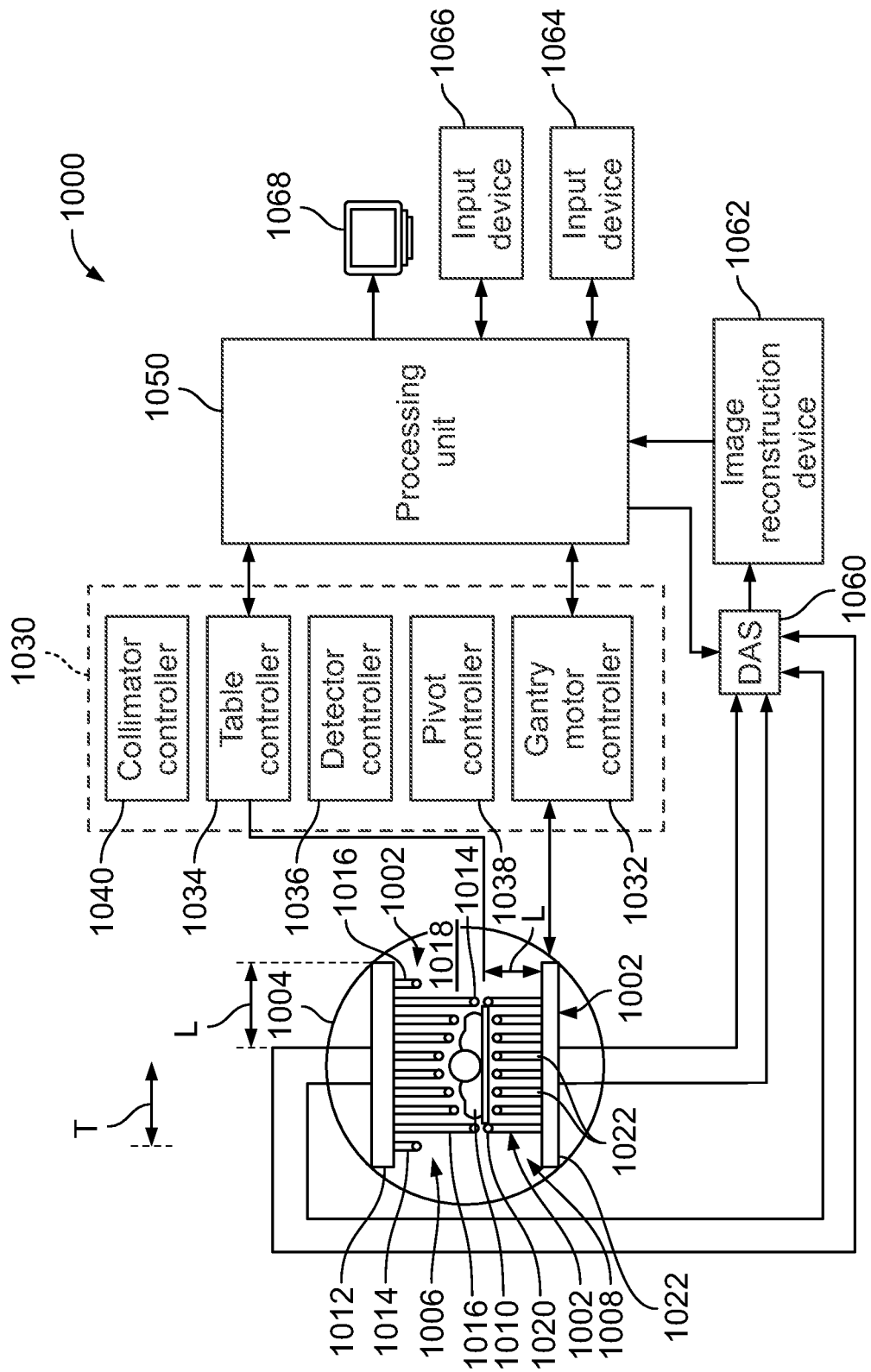
FIG. 12 shows a schematic view of an imaging system, according to an embodiment.

The embodiments described above and illustrated by other figures herein may be implemented in medical imaging systems, such as, for example, SPECT, SPECT-CT, PET and PET-CT. Various methods and/or systems (and/or aspects thereof) described herein may be implemented using a medical imaging system. For example, FIG. 12 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 12 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 12. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 12). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 12 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and further from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or pivot around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 12 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that system sensitivity depends on the number of detector units that are positioned in proximity to the patient and to the organ of interest within the patient. Thus, it may be an advantage to be able to closely position as many detector units near the patient and to the organ of interest. Having two closely packed detector units within one housing may be advantageous with respect to having two separate housings, as limiting each arm to having one detector unit per housing wall represents a "dead space" not utilized for detection. In addition, reducing the number of arms increase the reliability of the system.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A radiation detector assembly comprising:
a multi-detector arm having a base and an arm housing that extends radially from within the base, the arm housing defining a cavity therein, the arm housing configured to translate linearly towards and away from a patient;
between 2 and 5 detector head units disposed within the cavity of the multi-detector arm, each detector head unit comprising an absorption member and associated processing circuitry, the processing circuitry configured to generate electronic signals responsive to radiation received by the absorption member, wherein each detector head unit is configured to pivot along a sweep direction.

2. The radiation detector head assembly of claim 1, wherein the multi-detector arm comprises exactly two detector head units.

3. A radiation detection system comprising:
a gantry defining a bore, the gantry comprising a stator and a rotor, the rotor configured to rotate relative to the stator;
plural multi-detector arms radially disposed about the bore and mounted to the rotor, each multi-detector arm defining a cavity therein, each multi-detector arm having a distal portion and a base portion, the base portion mounted to the rotor, the distal portion extendable from the base portion; and
plural detector head units disposed within each of the plural multi-detector arms, each detector head unit disposed in the cavity in the distal portion of the corresponding multi-detector arm, each detector head unit comprising an absorption member and associated processing circuitry, the processing circuitry configured to generate electronic signals responsive to radiation received by the absorption member, wherein each detector head unit is configured to pivot along a sweep direction.

4. The radiation detection system of claim 3, further comprising single detector arms radially disposed about the bore and mounted to the rotor, each single detector arm having only a single detector head unit disposed therein.

5. The radiation detection system of claim 4, wherein at least some of the single detector arms alternate with multi-detector arms along a circumference of the rotor.

6. The radiation detection system of claim 5, comprising 6 multi-detector arms and 6 single detector arms arranged in an alternating layout along a circumference of the rotor.

7. The radiation detection system of claim 3, comprising 6 multi-detector arms evenly distributed about a circumference of the rotor.

8. The radiation detection system of claim 3, comprising 12 multi-detector arms evenly distributed about a circumference of the rotor.

9. The radiation detection system of claim 3, further comprising a non-rotating multi-detector housing that does not rotate with the rotor, the non-rotating multi-detector housing comprising at least two detector head units.

10. The radiation detection system of claim 9, further comprising a table disposed within the bore, the non-rotating multi-detector housing mounted to the table.

11. The radiation detection system of claim 9, wherein the non-rotating multi-detector housing is mounted to the stator.

12. The radiation detection system of claim 9, wherein the non-rotating multi-detector housing is configured to be adjustable along at least one linear direction.

13. A method including:
providing plural multi-detector arms, each multi-detector arm defining a cavity therein, each multi-detector arm having a distal portion and a base portion, the distal portion extendable from the base portion;
disposing plural detector head units in the cavity in the distal portion within each of the plural multi-detector arms, each detector head unit comprising an absorption member and associated processing circuitry, the processing circuitry configured to generate electronic signals responsive to radiation received by the absorption member, wherein each detector head unit is configured to pivot along a sweep direction; and
mounting the base portion of each of the plural multi-detector arms to a rotor of a gantry about a bore defined by the gantry, the gantry comprising a stator, the rotor configured to rotate relative to the stator.

14. The method of claim 13, further comprising mounting single detector arms to the rotor radially disposed about the bore, each single detector arm having only a single detector head unit disposed therein.

15. The method of claim 14, wherein at least some of the single detector arms alternate with multi-detector arms along a circumference of the rotor.

16. The method of claim 15, comprising mounting 6 multi-detector arms and 6 single detector arms arranged in an alternating layout along the circumference of the rotor.

17. The method of claim 13, comprising mounting 6 multi-detector arms evenly about a circumference of the rotor.

18. The method of claim 13, comprising mounting 12 multi-detector arms evenly about a circumference of the rotor.

19. The method of claim 13, further comprising mounting a non-rotating multi-detector housing comprising at least two detector head units to a table disposed within the bore.

20. The method of claim 13, further comprising mounting a non-rotating multi-detector housing comprising at least two detector head units to the stator of the gantry.

* * * * *